(12) United States Patent
Chang et al.

(10) Patent No.: US 6,607,487 B2
(45) Date of Patent: Aug. 19, 2003

(54) ULTRASOUND IMAGE GUIDED ACETABULAR IMPLANT ORIENTATION DURING TOTAL HIP REPLACEMENT

(75) Inventors: John Chang, Walnut Creek, CA (US); Waleed Haddad, San Francisco, CA (US); Jan-Ulco Kluiwstra, Oakland, CA (US); Dennis Matthews, Moss Beach, CA (US); Kenneth Trauner, Sacramento, CA (US)

(73) Assignee: The Regents of the University of California, Oakland, CA (US)

(*) Notice: Subject to any disclaimer, the term of this patent is extended or adjusted under 35 U.S.C. 154(b) by 144 days.

(21) Appl. No.: 09/767,454

(22) Filed: Jan. 23, 2001

(65) Prior Publication Data

US 2002/0099288 A1 Jul. 25, 2002

(51) Int. Cl.[7] ................................................. A61B 8/00
(52) U.S. Cl. ....................................................... 600/437
(58) Field of Search ................................. 600/437, 443, 600/444, 459, 447, 460, 426, 424, 407; 395/94; 364/413

(56) References Cited

U.S. PATENT DOCUMENTS

| 4,404,692 A | | 9/1983 | Eftekhar ..................... 3/1.912 |
|---|---|---|---|
| 5,086,401 A | * | 2/1992 | Glassman et al. ........... 700/259 |
| 5,402,801 A | | 4/1995 | Taylor ........................ 128/898 |
| 5,769,092 A | | 6/1998 | Williamson ................. 128/898 |
| 5,879,301 A | * | 3/1999 | Chiabrera et al. .......... 600/437 |
| 6,002,859 A | * | 12/1999 | DiGioia et al. ............... 703/11 |
| 6,256,529 B1 | * | 7/2001 | Holupka et al. ............ 600/427 |
| 6,370,418 B1 | * | 4/2002 | Bernoski ..................... 600/426 |
| 6,385,475 B1 | * | 5/2002 | Cinquin et al. ............. 600/407 |
| 6,413,215 B1 | * | 7/2002 | Wu et al. .................... 600/437 |
| 6,425,865 B1 | * | 7/2002 | Salcudean et al. .......... 600/111 |

FOREIGN PATENT DOCUMENTS

| WO | WO 99/59487 | 11/1999 | ........... A61B/17/58 |

\* cited by examiner

Primary Examiner—Francis J. Jaworski
Assistant Examiner—Maulin M Patel
(74) Attorney, Agent, or Firm—Eddie E. Scott; Alan H. Thompson

(57) ABSTRACT

A system for assisting in precise location of the acetabular implant during total hip replacement. The system uses ultrasound imaging for guiding the placement and orientation of the implant.

7 Claims, 3 Drawing Sheets

ULTRASOUND IMAGE GUIDED ACETABULAR IMPLANT ORIENTATION DURING TOTAL HIP REPLACEMENT

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to surgery, and in particular relates to precise location of an implant during surgery.

2. State of Technology

A report by the Office of Medical Applications of Research of the National Institutes of Health states that more than 120,000 artificial hip joints are being implanted annually in the United States. Successful replacement of deteriorated, arthritic, and severely injured hips has contributed to enhanced mobility and comfortable, independent living for many people who would otherwise be substantially disabled. New technology involving prosthetic devices for replacement of the hip, along with advances in surgical techniques, has diminished the risks associated with the operation and improved the immediate and long-term outcome of hip replacement surgery.

Primary total hip replacement (THR) is most commonly used for hip joint failure caused by osteoarthritis; other indications include, but are not limited to, rheumatoid arthritis, avascular necrosis, traumatic arthritis, certain hip fractures, benign and malignant bone tumors, the arthritis associated with Paget's disease, ankylosing spondylitis, and juvenile rheumatoid arthritis. The aims of THR are relief of pain and improvement in function.

Improvement can still be made however, concerning prosthetic and operating designs and materials that are most effective for specific groups of patients and which surgical techniques and rehabilitation approaches yield the best long-term outcomes. Issues also exist regarding the best indications and approaches for revision surgery.

PCT publication WO 99/59487, titled An Acetabular Total Hip Component Alignment System for Accurate Intraoperative Positioning in Inclination, by William A. McGann, published Nov. 25, 1999, provides the following description: "An alignment system is used for alignment structure for surgical procedures. The alignment system and method can be used in a preferred embodiment to align an acetabular cup implant for purposes of a hip replacement procedure. The alignment system and method can be used for other alignment procedures whether or not an implant is utilized.

U.S. Pat. No. 6,002,859, titled Apparatus and Method Facilitating the Implantation of Artificial Components in Joints, to Michael K. Blackwell, Anthony M. DiGioia III, Branislav Jaramaz, Takeo Kanade, Frederick M. Morgan, Robert V. O'Toole, and David A. Simon, assigned to Carnegie Mellon University, patented Dec. 14, 1999, provides the following description: "Apparatuses and methods are disclosed for determining an implant position for at least one artificial component in a joint and facilitating the implantation thereof. The apparatuses and methods include creating a joint model of a patient's joint into which an artificial component is to be implanted and creating a component model of the artificial component. The joint and artificial component models are used to stimulate movement in the patient's joint with the artificial component in a test position. The component model and the joint model are used to calculate a range of motion in the joint for at least one test position based on the simulated motion. An implant position, including angular orientation, in the patient's joint is determined based on a predetermined range of motion and the calculated range of motion. In a preferred embodiment, the implant position can be identified in the joint model and the joint model aligned with the joint by registering positional data from discrete points on the joint with the joint model. Such registration also allows for tracking of the joint during surgical procedures. A current preferred application of the invention is for determining the implant position and sizing of an acetabular cup and femoral implant for use in total hip replacement surgery."

U.S. Pat. No. 5,769,092, titled Computer-aided system for revision total hip replacement surgery, issued Jun. 23, 1998, to Willie Williamson, Jr., assigned to Integrated Surgical Systems, Inc., provides the following description: "computer implemented systems and methods for removing bone cement or other material to replace a bone prosthesis is provided. A computer aided method of replacing a bone prosthesis according to the present invention comprises the steps of: receiving as input image data of a bone; identifying bounding contours of material in the image data surrounding a first bone prosthesis for removal; and generating system contours from the bounding contours, the system contours specifying a cavity to be cut in the bone to accommodate a second bone prosthesis."

U.S. Pat. No. 5,402,801, titled System and method for augmentation of surgery, issued Apr. 4, 1995, to Russell H. Taylor, assigned to International Business Machines Corporation, provides the following description: "The system and method includes a manipulator for manipulating a surgical instrument relative to a patient's body and, a position sensor for sensing the position of the surgical instrument relative to the patient's body. The manipulator can be manually or computer actuated and can have brakes to limit movement. In a preferred embodiment, orthogonal only motion between members of the manipulator is provided. The position sensor includes beacons connected to the patient and manipulator or surgical instrument and, a three dimensional beacon sensor adapted to sense the location and position of the beacons. Redundant joint sensors on the manipulator may also be provided. The system and method uses a computer to actively interact with the surgeon and can use various different input and output devices and modes."

U.S. Pat. No. 4,404,692 for a centering system for hip replacement, by Nas S. Eftekhar, patented Sep. 20, 1983, provides the following description: "The present invention provides a system for centering proximally and distally a hip replacement. The system comprises a trial hip prosthesis for centering proximally the hip replacement and a device adapted for insertion into the medullary canal for centering distally the hip replacement, the device being provided with means to receive and center the stem in the hip replacement. A method for obtaining a proximally and distally centered total replacement is also provided."

SUMMARY OF THE INVENTION

A system for assisting in precise location of an implant during surgery. The system uses ultrasound imaging for guiding the placement and orientation of the implant. The target area is interrogated using ultrasound. Reference points are marked relative to the target area. The reference points are used to locate the implant in the target area. Additional aspects, advantages, and features of the invention are set forth in part in the following description. Various aspects, advantages, and features of the invention will become apparent to those skilled in the art upon examination of the description and by practice of the invention.

BRIEF DESCRIPTION OF THE DRAWINGS

The accompanying drawings, which are incorporated into and form a part of the disclosure, illustrate embodiments of the invention, and, together with the description, serve to explain the principles of the invention.

DETAILED DESCRIPTION OF THE INVENTION

Figure 2:
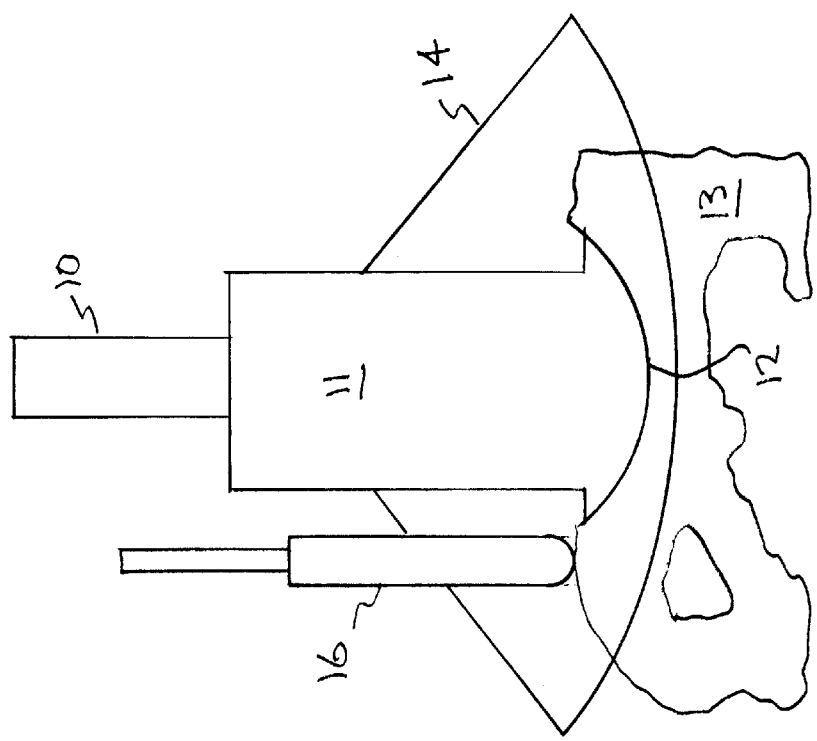
FIG. 2 shows the aetabulum cavity after reaming with the alignment markings being placed on the rim of the socket.

The Surgical Procedure. The steps involved in replacing the hip begin with making an incision about 8 inches long over the hip joint. There are several different approaches used to make the incision, usually based on the surgeon's training and preferences.

After the incision has been made, the ligaments and muscles are separated to provide the surgeon access to the bones of the hip joint. It is this part of the surgery that makes the ligaments and muscles somewhat weak after surgery. Until they heal, which takes about a month to six weeks, the patient must follow special hip precautions to prevent dislocation of the patient's new hip joint.

Once the hip joint is entered, the femoral head is dislocated from the acetabulum. Then the femoral head is removed by cutting through the femoral neck with a power saw.

After the femoral head is removed, the cartilage is removed from the acetabulum using a power drill and a special reamer. The reamer forms the bone in a hemispherical shape to exactly fit the metal shell of the acetabular component.

A trial component, which is an exact duplicate of the patient's hip prosthesis, is used to ensure that the joint the patient receives will be the right size and fit for the patient. Once the right size and shape is determined for the acetabulum, the acetabular component is inserted into place. In the uncemented variety of artificial hip replacement, the metal shell is simply held in place by the tightness of the fit or with screws to hold the metal shell in place. In the cemented variety, a special epoxy type cement is used to "glue" the acetabular component to the bone.

To begin replacing the femoral head, special rasps are used to shape and hollow out femur to the exact shape of the metal stem of the femoral component. Once again, a trial component is used to ensure the correct size and shape. The surgeon will also test the movement of the hip joint.

Once the size and shape of the canal exactly fit the femoral component, the stem is inserted into the femoral canal. Again, in the uncemented variety of femoral component the stem is held in place by the tightness of the fit into the bone (similar to the friction that holds a nail driven into a hole drilled into wooden board—with a slightly smaller diameter than the nail). In the cemented variety, the femoral canal is rasped to a size slightly larger than the femoral stem. Then the epoxy type cement is used to bond the metal stem to the bone.

The metal ball that replaces the femoral head is attached to the femoral stem.

The patient now has a new weight bearing surface to replace the patient's diseased hip. Before the patient's incision is closed, an x-ray (image) is made to make sure the patient's new prosthesis is in the correct position.

An Embodiment of the Present Invention. To assist the orthopedic surgeon in precise location of the acetabular implant during total hip replacement, an embodiment of the present invention provideds a system which uses ultrasound imaging for guiding the placement and orientation of the implant relative to the anatomical landmarks surrounding the acetabulum such as the greater sciatic notch, the spine of the ischium, gemellus superior, obturator foramen, the anterior inferior spine and others.

This system helps eliminate one of the major causes of the failure of hip prostheses, misalignment leading to abnormal wear rate for the implant or improper seating of the implant leading to restricted leg movement and frequent hip separation. The system is applicable to hip joint replacement surgical procedures performed in VA hospitals and any application requiring macroscopic image guidance of high reflective targets through materials with low ultrasonic impedance. The system is potentially useful for every hip replacement surgery performed worldwide.

The embodiment of the present invention provides a means for the surgeon to orient the implant relative to recognizable ultrasound images of the surface of the pelvic bone. The embodiment of the present invention includes three parts. The first part consists of an ultrasonic imaging head used for real-time, in-vivo imaging of the pelvic region during hip joint replacement procedures. The imager is used to interrogate the pelvic bone. Specifically, the imager surveys the bone structure surrounding the acetabulum by:

1) transmitting ultrasound signals through layers of muscle, fat, tendons, ligaments, and surrounding vasculature either with or without the use of a coupling bolus;

2) transmitting ultrasound signals using a phased array of transducers through the acetabular surface into the bone and image the outer surface of the hip bone from within; or 3) transmitting ultrasound signals using a phased linear array transducers straddling the rim of the acetabular.

The second part consists of an ultrasonic adapter cup attached to the end of the imaging head. This acetabulum cup adapter precisely matches the shape of the acetabulum using the ultrasonic imaging head described above. The adapter is detachable from the imaging head and can accept a standard insertion stem used in hip joint replacement procedures for marking reference points directly onto the hip bone. The adapter is made of an ultrasonic transparent material in a hemispherical shape. The marking can be done through a standard milling or drilling technique typically used during a hip replacement procedure. Once the hipbone has these landmarks, the adapter is removed leaving the acetabulum with only the landmarks present. The orthopedic surgeon then accurately places the permanent acetabular component using these landmarks.

The third part consists of a specialized image processing tool that will provide real time imaging of the acetabulum region.

Figure 1:
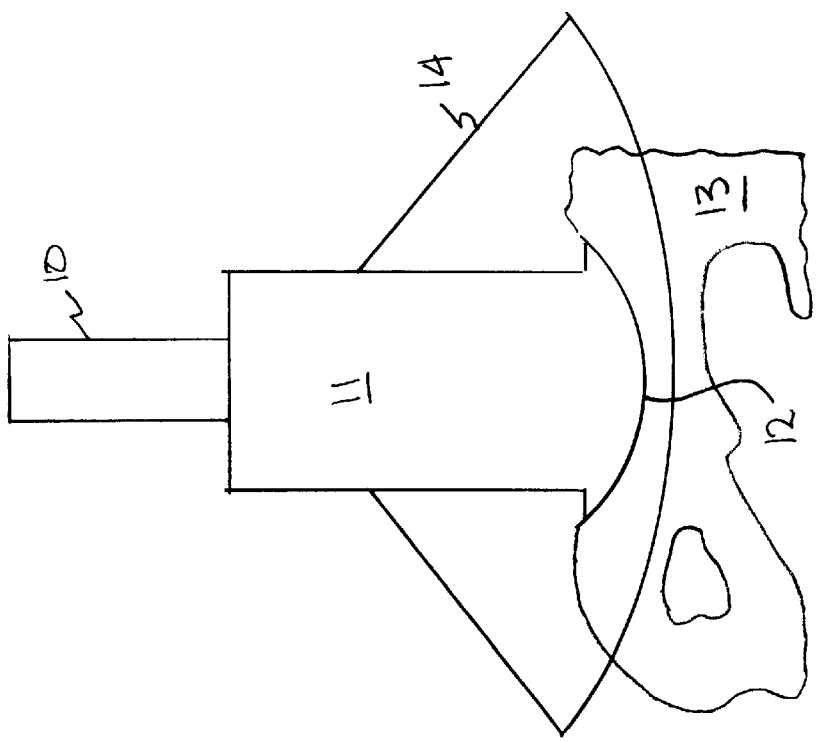
FIG. 1 shows a part of the pelvis bone after the reaming procedure.

A part of the pelvis bone 13 after the reaming procedure is shown in FIG. 1. The ultrasound scan head 10 is placed on top of the (disposable) acoustic coupling adapter 11 that is placed in the joint socket 12. The ultrasound image 14 includes the joint socket (Acetabulum) 12, the upper part (crest of the Ilium) and the lower part (Ischium) of the hipbone giving the appropriate reference points and orientation to aid surgeons in the cup alignment.

Figure 4:
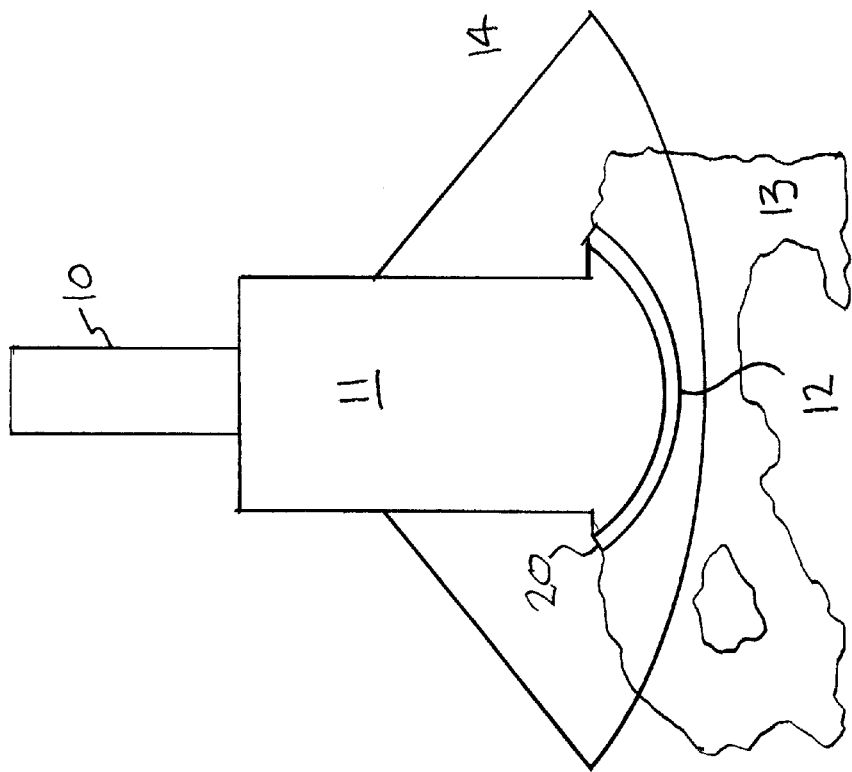
FIG. 4 shows the cup is in position wherein the edges of the cup line up with the alignment marking indicating correct placement of the cup.
Figure 3:
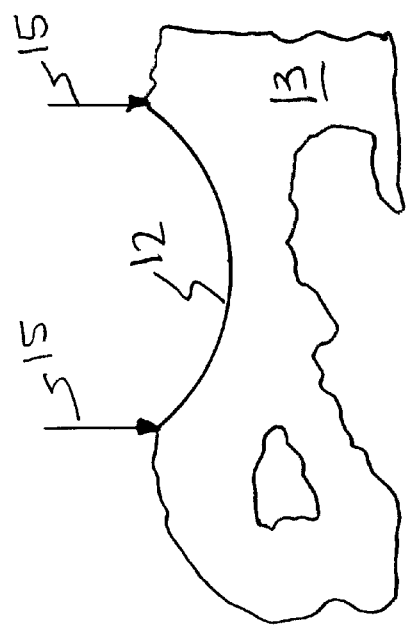
FIG. 3 shows the markers used to line-up the permanent cup.

Once the acoustic coupling adapter 11 is put in place, small alignment markings 15 are made on the bony edge of the joint rim. FIG. 2 shows a drill and grinding tool 16 positioned adjacent the ultrasound scan head 10 and acoustic coupling adapter 11. FIG. 3 shows the small alignment markings 15 on the bony edge of the joint rim. The markers 15 are used later on to line-up the permanent cup. In FIG. 4 the cup 11 is in position, the edges of the cup line up with the alignment marking indicating correct placement of the cup 11.

Ultrasound imaging. Ultrasound imaging aids during placement of the acetabulum component in hip replacement surgery. During the procedure ultrasound imaging can be used to identify prominent anatomical features offering reference points during the placement of the cup. A commercial available ultrasound imaging system can be fitted with acoustic coupling adapter for direct placement of Acetabulum component in hip replacement surgery.

Alignment procedure. After a reaming tool prepares the joint socket for the Acetabulum component ('cup') a dummy alignment cup is inserted in the socket. This dummy cup has coupling medium for the ultrasound imager and drill guides to make small ridges (alignment markings) in the socket edge. These small ridges will aid with the correct placement of the permanent cup. Making ridges in at least three places will ensure correct alignment.

Acoustic Coupling Adapter. The acoustic coupling adapter couples the acoustic energy in the bone and surrounding tissue allowing to image the region of interest. The front end of the acoustic coupler is shaped to fit the reamed (prepared) joint socket similar to the shape of the permanent cup.

Figure 5:
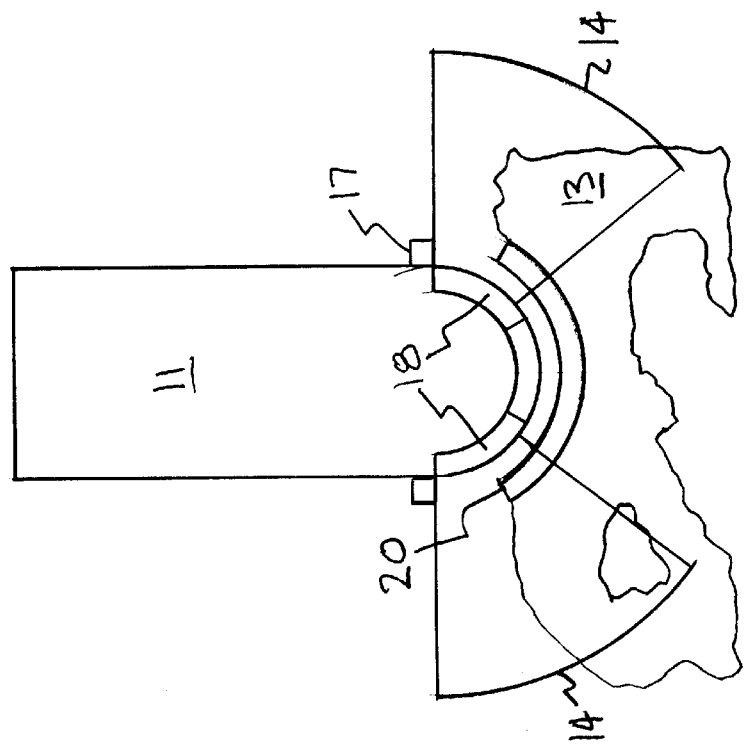
FIG. 5 shows two arrays placed on a sphere where each array is looking sideways at the junction between the cup, bone and soft tissue surrounding the joint.

Transducer Design: Split Side View Arrays. The second design, shown in FIG. 5, consists of two arrays 18 placed on a sphere where each array is looking sideways at the junction between the cup, bone and soft tissue surrounding the joint. The acoustic coupling adapter 17 couples the acoustic energy in the bone and surrounding tissue allowing to image the region of interest. The two arrays 18 are rotated inside the socket to view the complete joint socket and neighboring tissues.

Figure 6:
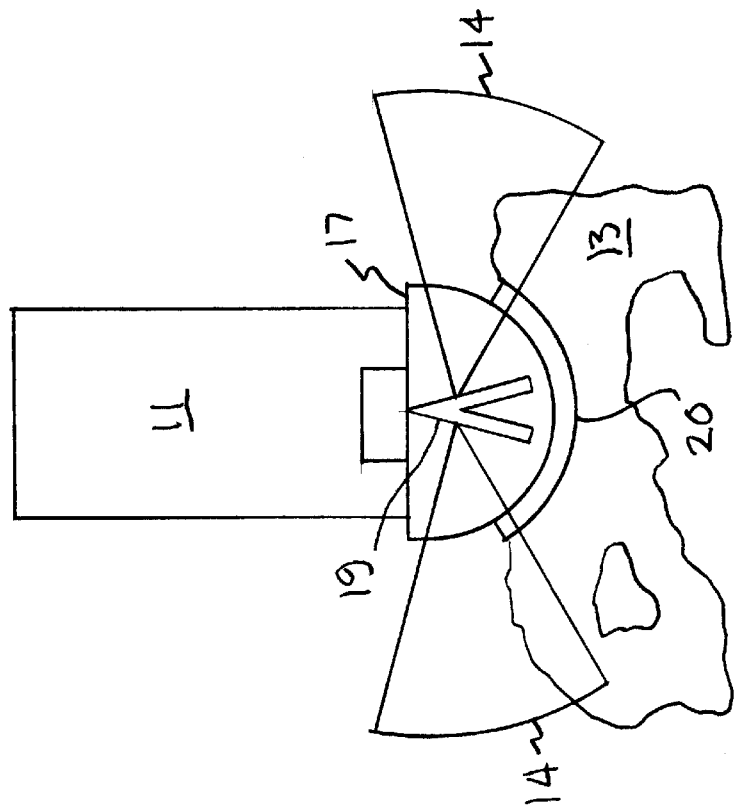
FIG. 6 shows a conventional ultrasound phased array.

Transducer design: Conventional Ultrasound Phased Array. The third design, shown in FIG. 6, involves a conventional ultrasound phased array. The split view is obtained by using two reflecting surfaces 19 to look sideways. This offers an added advantage of using standard ultra sound scan heads. Specialized reconstruction algorithms will be use to display; the imaged obtained with this design.

Visualization software. Visualization software is used to display the images from the designs depicted in FIG. 5 and in FIG. 6. The visualization will allow surgeons to visualize the joint socket in separate 2-dimensional images or in 3-dimensional volumetric imaging. This imaging procedure will ensure correct alignment of the cup in the joint socket.

What is claimed is:

1. A surgical method for assisting a surgeon in precise location of an acetabular implant during total hip replacement by positioning said acetabular implant in a patient's joint socket in said patient's pelvic region, comprising the steps of:

interrogating said patient's pelvic region using an ultrasound imaging head, positioning an ultrasonic adapter cup in said patient's joint socket and located between said ultrasopic imaging head and said patient's pelvic region, marking reference alignment markings in said patient's joint socket relative to said patient's pelvic region, and using said reference alignment markings to locate said ultrasonic adapter cup and said acetabular implant in said patient's joint socket during total hip replacement.

2. The surgical method of claim 1, wherein in said step of interrogating said patient's pelvic region using an ultrasonic imaging head, said ultrasonic imaging head is used for real-time in-vivo imaging of said patient's pelvic region.

3. The surgical method of claim 1 wherein in said step of marking reference alignment markings in said patient's joint socket relative to said patient's pelvic region, milling or drilling is used to mark said reference alignment markings relative to said patient's pelvic region.

4. The surgical method of claim 3 wherein real time imaging is used in said step of marking reference alignment markings in said patient's joint socket relative to said patient's pelvic region to locate said acetabular implant in in said patient's joint socket during total hip replacement.

5. An apparatus to assist a surgeon in precise location of an acetabular implant during total hip replacement by positioning said acetabular implant in a patient's joint socket in said patient's pelvic region, comprising:

an ultrasonic imaging head for real-time in-vivo imaging of said patient's joint socket and pelvic region during hip joint replacement, an ultrasonic adapter cup operatively connected to said ultrasonic imaging head, said ultrasonic adapter cup having a portion that fits within said joint socket, and alignment markings operatively positioned in said joint socket for accurate positioning of said ultrasonic adapter cup and said acetabular implant in said joint socket.

6. The apparatus of claim 5 wherein said ultrasonic adapter cup portion that fits within said joint socket substantially matches the shape of said joint socket and said acetabulum.

7. The apparatus of claim 5 including a drill operatively connected to said ultrasonic imaging head and said ultrasonic adapter cup that operates to operatively position said alignment markings in said joint socket.

* * * * *